United States Patent
LaFont et al.

(10) Patent No.: US 9,283,094 B2
(45) Date of Patent: Mar. 15, 2016

(54) POLYMER-BASED STENT ASSEMBLY

(75) Inventors: Antoine LaFont, Paris (FR); Serge Piranda, Besancon (FR); Patrick Sabaria, Saint Nom la Breteche (FR); Tahmer Sharkawi, Saint Jean de Vedas (FR); Michel Vert, Castelnau-le-Lez (FR)

(73) Assignee: Arterial Remodelling Technologies, Inc. (FR)

( * ) Notice: Subject to any disclaimer, the term of this patent is extended or adjusted under 35 U.S.C. 154(b) by 567 days.

(21) Appl. No.: 12/764,447

(22) Filed: Apr. 21, 2010

(65) Prior Publication Data

US 2010/0204778 A1  Aug. 12, 2010

Related U.S. Application Data

(62) Division of application No. 10/508,739, filed as application No. PCT/EP2004/004133 on Apr. 2, 2004, now Pat. No. 7,731,740.

(51) Int. Cl.

| A61F 2/06 | (2013.01) |
| A61F 2/82 | (2013.01) |
| A61L 31/06 | (2006.01) |
| A61F 2/958 | (2013.01) |
| A61F 2/95 | (2013.01) |

(52) U.S. Cl.
CPC . *A61F 2/82* (2013.01); *A61L 31/06* (2013.01); *A61F 2/958* (2013.01); *A61F 2002/9522* (2013.01); *A61F 2210/0004* (2013.01)

(58) Field of Classification Search
CPC .................................. A61F 2/82; A61F 2/94
USPC ................................ 623/1.11, 1.15
See application file for complete search history.

(56) References Cited

U.S. PATENT DOCUMENTS

| 4,950,258 A | 8/1990 | Kawai et al. |
| 5,163,952 A | 11/1992 | Froix |
| 5,258,020 A | 11/1993 | Froix |
| 5,423,885 A | 6/1995 | Williams |
| 5,607,467 A | 3/1997 | Froix |
| 5,670,161 A * | 9/1997 | Healy et al. ............... 623/1.42 |
| 5,716,410 A | 2/1998 | Wang et al. |
| 5,766,710 A | 6/1998 | Turnlund et al. |
| 5,827,322 A | 10/1998 | Williams |
| 5,957,975 A | 9/1999 | LaFont et al. |
| 5,980,551 A | 11/1999 | Summers et al. |
| 6,022,371 A | 2/2000 | Killion |
| 6,080,177 A | 6/2000 | Igaki et al. |
| 6,160,084 A | 12/2000 | Langer et al. |
| 6,228,845 B1 | 5/2001 | Donovan et al. |
| 6,248,129 B1 | 6/2001 | Froix |
| 6,338,739 B1 | 1/2002 | Datta et al. |
| 6,388,043 B1 | 5/2002 | Langer et al. |
| 6,485,512 B1 | 11/2002 | Cheng et al. |
| 6,527,801 B1 | 3/2003 | Dutta |
| 6,537,312 B2 | 3/2003 | Datta et al. |
| 6,592,895 B2 | 7/2003 | Lang et al. |
| 6,736,842 B2 | 5/2004 | Healy et al. |
| 7,572,287 B2 * | 8/2009 | Stinson ..................... 623/1.15 |
| 7,731,740 B2 | 6/2010 | LaFont et al. |
| 2002/0087165 A1 | 7/2002 | Lee et al. |
| 2002/0183830 A1 | 12/2002 | Su et al. |
| 2002/0188346 A1 | 12/2002 | Healy et al. |
| 2002/0193336 A1 | 12/2002 | Elkins et al. |
| 2003/0055488 A1 | 3/2003 | Igaki |
| 2003/0216804 A1 | 11/2003 | DeBeer et al. |
| 2004/0034405 A1 | 2/2004 | Dickson |

(Continued)

FOREIGN PATENT DOCUMENTS

| EP | 0809981 | 12/1997 |
| WO | 03/034940 | 5/2003 |
| WO | 2005/096992 | 10/2005 |

OTHER PUBLICATIONS

Office action from U.S. Appl. No. 10/508,739 dated Dec. 13, 2007.

(Continued)

*Primary Examiner* — Gregory Anderson
(74) *Attorney, Agent, or Firm* — Tarolli, Sundheim, Covell & Tummino LLP

(57) ABSTRACT

Methods for preparing a polymer-based stent assembly comprising an inflatable balloon catheter and a polymer-based stent resistant to relaxation-related negative recoil are provided. The methods comprise heating a polymeric cylindrical device which is at a final predetermined shape and diameter to a temperature sufficiently above the glass transition temperature (Tg) of the polymer and for a time sufficient to erase any memory of previous processing of the polymeric cylindrical device and then quenching the polymeric cylindrical device to provide an educated polymeric cylindrical device having a memory of the final predetermined diameter and shape, mounting the educated cylindrical device on an inflatable balloon catheter, reducing the diameter of the educated cylindrical device by heating to a temperature at or slightly above the Tg of the polymer while evenly applying pressure on the exterior surface of the wall of the cylindrical device, and then cooling the cylindrical device below the Tg of the polymer to provide a stent assembly comprising an inflatable balloon catheter and an expandable, educated, polymeric stent snugly and stably disposed thereon. Assemblies comprising an inflatable balloon and a polymer based stent that is substantially resistant to relaxation related recoil mounted snugly on the balloon are also provided.

3 Claims, No Drawings

(56) References Cited

U.S. PATENT DOCUMENTS

2004/0045645 A1* 3/2004 Zhou .............................. 148/597
2005/0010275 A1* 1/2005 Sahatjian et al. ............ 623/1.11

OTHER PUBLICATIONS

Response from U.S. Appl. No. 10/508,739 dated Apr. 9, 2008.
Office action from U.S. Appl. No. 10/508,739 dated Jul. 15, 2008.
Response from U.S. Appl. No. 10/508,739 dated Dec. 12, 2008.
Office action from U.S. Appl. No. 10/508,739 dated Mar. 26, 2009.
Response from U.S. Appl. No. 10/508,739 dated Jun. 25, 2009.
Notice of Allowance from U.S. Appl. No. 10/508,739 dated Jan. 27, 2010.
International Search Report and Written Opinion from PCT/EP04/004133 dated Dec. 30, 2004.
LaFont, et al., "Restenosis After Experimental Angioplasty", Circulation Research, 76: 966-1002 (1995).
Communication from European Application No. 04725381.0 dated Apr. 3, 2007.
Response from European Application No. 04725381.0 dated Oct. 8, 2007.
Communication from European Application No. 04725381.0 dated Dec. 13, 2007.
Response from European Application No. 04725381.0 dated Apr. 10, 2008.
Communication from European Application No. 04725381.0 dated Jun. 16, 2008.
Response from European Application No. 04725381.0 dated Dec. 9, 2008.
Odian, G., "Principles of Polymerization," Fourth Edition, Wiley-Interscience, p. 26 (2004).
Mark, J.E., ed., "Polymer Data Handbook," Oxford University Press, Inc., pp. 566-569; 627-633 (1999).
Barbanti et al., "Effect of Salt Leaching on PCL and PLGA (50/50) Resorbable Scaffolds", Materials Research, vol. 11, No. 1, pp. 75-80 (2008).
Franco, et al., "Comparative Thermal Degradation Studies on Glycolide/Trimethylene Carbonate and Lactide/Trimethylene Carbonate Copolymers", J. of Applied Polymer Science, vol. 104, pp. 3539-3553 (2007).
Valimaa, et al., "Viscoelastic memory and self-expansion of self-reinforced bioabsorbable stents", Biomaterials, 23 (2002) 3575-3582.
Wache, et al., "Development of a polymer stent with shape memory effect as a drug delivery system", Journal of Materials Science: Materials in Medicine, 14 (2003) 109-112.
Lendlein, et al., "Biodegradable, Elastic Shape-Memory Polymers for Potential Biomedical Applications", Science, vol. 296 May 31, 2002, pp. 1673-1676.
Eberhart, et al., "Bioresorbable polymeric stents: current status and future promise", J. Biomater. Sci. Polymer Edn, vol. 14, No. 4, pp. 299-312 (2003).
Tsuji, et al., "Biodegradable Polymeric Stents", Curr. Interv. Cardiol. Rep., 3(1): 10-17 (2001).
Zeltinger, et al., "Advances in the Development of Coronary Stents", Biomaterials Forum, (2004).
Su, et al., "Expandable Bioresorbable Endovascular Stent. I. Fabrication and Properties", Annals of Biomedical Engineering, vol. 31, pp. 667-677, 2003.

* cited by examiner

POLYMER-BASED STENT ASSEMBLY

CROSS REFERENCE TO RELATED APPLICATIONS

This application is a divisional application of and claims priority to U.S. patent application No. 10/508,739, filed on Dec. 30, 2004, titled "POLYMER-BASED STENT ASSEMBLY," which in turn claims priority to International Patent Application No. PCT/EPO4/004133, filed Apr. 2, 2004, both of which are hereby incorporated by reference in their entirety.

FIELD OF THE INVENTION

The present invention relates to a polymer-based stent assembly comprising an inflatable balloon catheter and a polymer-based stent for maintaining the shape of a tube, duct, or vessel, including, but not limited to, a urethral duct, a biliary duct, a blood vessel, a lymph vessel, a bronchial tube, or a duct in the prostate of a mammalian subject, preferably a human subject. More particularly, the present invention relates to an assembly comprising a degradable polymeric stent that exhibits little to no relaxation-related negative recoil when implanted in a tube, duct or vessel of a mammalian subject.

BACKGROUND

Atherosclerosis is a disease in which vascular lesions or plaques consisting of cholesterol crystals, necrotic cells, lipid pools, excess fiber elements and calcium deposits accumulate on the interior walls of an individual's arteries. The presence of such plaques in the artery leads to thickening of the arterial wall and narrowing of the lumen. Eventually the enlargement of such plaques can lead to an occlusion of the lumen of the artery at the site of the lesion. One of the most successful procedures for treating atherosclerosis of the coronary arteries is percutaneous transluminal coronary angioplasty, hereinafter referred to as "PTC angioplasty". PTC angioplasty consists of introducing a deflated balloon into the lumen of the atherosclerotic artery, placing the balloon adjacent the site of the plaque or atherosclerotic lesion, inflating the balloon to a pressure of approximately 6 to 20 atmospheres thereby "cracking" the plaque and increasing the cross-sectional area of the lumen of the artery.

Unfortunately, the pressure that is exerted on the plaque during PTC angioplasty also traumatizes the artery. Accordingly, in 30-40% of the cases the vessel either gradually renarrows or recloses at the locus of the original stenotic lesion. This gradual renarrowing or reclosure, which is hereinafter referred to as "chronic restenosis," is a phenomenon that occurs almost exclusively during the first three to six months following angioplasty. Studies of the mechanism of chronic restenosis have shown that it is due in large part to a chronic constriction of the artery at the site of the barotraumatization, hereinafter referred to as the "retractile form of restenosis", and to a lesser extent to a proliferation of smooth muscle cells, hereinafter referred to as the "proliferative form of restenosis". Lafont et al. (1995) Restenosis After Experimental Angioplasty, Circulation Res. 76:996-1002.

A number of approaches for preventing restenosis are currently being used or tested. One approach involves the use of bioactive agents to prevent proliferation of the smooth muscle cells. To date, the use of bioactive agents alone has proven to be unsuccessful. Another approach employs a metallic stent which is deployed at the site of the stenotic lesion following PTC angioplasty. Although metallic stents have the mechanical strength necessary to prevent the retractile form of restenosis, their presence in the artery can lead to biological problems including vasospasm, compliance mismatch, and even occlusion. Occasionally, technical difficulties, including distal migration and incomplete expansion, have also been observed with metallic stents. Moreover, there are inherent, significant risks from having a metal stent permanently implanted in the artery, including erosion of the vessel wall. In addition, the constant exposure of the stent to the blood can lead to thrombus formation within the blood vessel.

Stents made from degradable polymers have also been suggested for preventing restenosis. Although, generally an attractive alternative to metallic stents, testing in animals has shown that degradable stents still suffer from multiple complications, including relaxation-related negative recoil and distal migration of the entire stent or portions thereof and formation of an occlusive thrombus within the lumen of the stent.

Accordingly, it is desirable to have a new stent that overcomes the disadvantages of the current stent designs. A polymer-based stent that exhibits little to no relaxation-related negative recoil when implanted in the blood vessel or duct of a mammalian subject is desirable. It is also desirable to have a stent assembly comprising an inflatable balloon catheter, and a degradable polymeric stent that is stably and snugly disposed thereon. A polymer-based stent assembly that does not require a mechanical restraint to prevent the stent from expanding when stored at room temperature or when exposed to the physiological conditions found in the bloodstream of a human patient are especially desirable. Methods of preparing such stents and stent assemblies are also desirable.

SUMMARY OF THE PRESENT INVENTION

The present invention provides methods for preparing a polymer-based stent assembly comprising an inflatable balloon catheter and a polymer-based stent resistant to relaxation-related negative recoil when implanted in the lumen of a blood vessel or duct of a mammalian subject, particularly a human subject. The polymer-based stent is in the form of a hollow cylindrical device comprising a wall formed from a polymer, preferably a degradable and bioresorbable polymer. Such wall defines a first open end, a second open end, and a channel extending from the first to the second open end, and has incorporated therein open spaces or slits that allow for a reduction in diameter and an increase in diameter of the cylindrical device without substantially altering the thickness of the wall.

In one aspect, the method comprises heating a polymeric cylindrical device which is at a final predetermined shape (i.e., the final desired diameter, wall thickness, length, and design of the stent following expansion) to a temperature sufficiently above the glass transition temperature (Tg) of the polymer and for a time sufficient to erase any memory of previous processing of the polymeric cylindrical device, and then quenching the polymeric cylindrical device, i.e., rapidly cooling the cylindrical device at a temperature below the Tg of the polymer, to provide an educated polymeric cylindrical device having a memory of the final predetermined diameter and shape (a procedure referred to hereinafter as "educating the cylindrical device"). Preferably, the polymeric cylindrical device is mounted on and in contact with a support during such education procedure. Thereafter, the method comprises mounting the educated cylindrical device on an inflatable balloon catheter, reducing the diameter of the educated cylindrical device by heating to a temperature at or slightly above the Tg of the polymer while evenly applying pressure on the exterior surface of the wall of the cylindrical device (a step referred to hereinafter as "crimping the cylindrical device"), and then cooling the cylindrical device below the Tg of the polymer to provide a stent assembly comprising an inflatable balloon catheter and an expandable, educated, polymeric stent snugly and stably disposed thereon. Slits or open spaces which allow for a reduction in diameter of the cylindrical device without substantially altering the wall thickness during crimping are incorporated into the cylindrical device prior to the time the cylindrical device is crimped on the inflatable balloon catheter. The temperature at which the cylindrical device is heated during crimping is high enough to allow reduction in diameter of the cylindrical device but low enough to not erase the memory of the final predetermined shape and diameter of the educated cylindrical device. Thus, the temperature at which the educated cylindrical device is heated during crimping is less than the temperature at which the cylindrical device is heated during education of the cylindrical device. In addition, the time during which the cylindrical device is heated during crimping is less than the time during which the cylindrical device is heated during education of the cylindrical device. In accordance with the present method, expansion of the polymeric stent to its final predetermined shape can be achieved either by inflating the balloon catheter on which the polymeric stent is disposed at body temperature, or by inflating the balloon catheter on which the polymeric stent is disposed while heating the stent to a temperature close to but not above the Tg of the polymer.

In another aspect, the method of the present invention starts with a polymeric tube whose diameter initially is less than the final predetermined diameter. Such tube, which also has slits or open spaces in the wall to allow expansion of the tube without substantially altering the diameter of the tube is first heated to a temperature close to or above the Tg of the polymer and expanded to provide a cylindrical device whose diameter is equal to the final desired diameter. Thereafter the cylindrical device is educated as described above to provide an educated cylindrical device having a memory of the final predetermined shape and diameter, and then crimped on a balloon catheter as described above to provide an assembly comprising the balloon catheter and an expandable, educated, polymeric stent snugly and stably disposed thereon.

The present invention also provides an assembly comprising an inflatable balloon catheter and a polymeric stent prepared in accordance with the present method.

In another aspect, the present invention relates to an assembly comprising an inflatable balloon catheter and a polymer-based stent mounted thereon. The stent is a cylindrical device formed from a degradable and bioresorbable polymeric material having a Tg at least 8 degrees greater than 37° C., preferably more than 20 degrees C. above 37° C., more preferably from about 45 to about 120 degrees C. The cylindrical device comprises a wall defining a first open end, a second open end, and a channel extending from the first open end to the second open end. The wall has voids or open spaces incorporated therein that allow the cylindrical device to be expanded to a larger diameter and substantially the same wall thickness when the balloon catheter is inflated or when the cylindrical device is heated to a temperature above the Tg of the polymer. Advantageously, the stent of the present invention exhibits little to no relaxation-related negative recoil when deployed in the blood vessel of a subject or when expanded to the final predetermined shape and diameter and stored at 37° C. for 4-6 weeks or more. Advantageously, the assembly of the present invention has a diameter which allows it to be easily inserted into a blood vessel of the subject and advanced to a target site. Advantageously, the stent of the present invention exhibits expansion (positive recoil) and adaptation to the geometry of the artery when the stent is not fully deployed up to its final diameter during deployment. In addition, the stent of the present invention is stably disposed on the balloon, meaning that a mechanical restraint is not required to prevent the stent from rapidly expanding to its final diameter during storage at room temperature. Thus, although not required, the assembly of the present invention, optionally, also comprises a retractable sheath covering the exterior surface of the stent. Such sheath serves to prevent deformation of the stent and slow expansion during storage.

The present invention also relates to methods of making stents lacking a memory of previous processing and having a memory of a final predetermined shape and diameter, and to stents made by such methods. Such stents exhibit little to no relaxation-related recoil when implanted in the lumen of a duct, vessel, or tube of a mammalian subject.

The present invention also relates to a method of reducing the risk of chronic restenosis that can occur in an artery of a patient following PTC angioplasty. The method employs the assembly of the present invention The method comprises delivering the stent assembly of the present invention to the locus of a stenotic lesion; inflating the balloon catheter to expand the stent to a diameter equal to or less than the final predetermined diameter such that the stent contacts or slowly expands to contact the interior walls of the blood vessel at the locus of the stenotic lesion; and then deflating and withdrawing the balloon catheter. In accordance with the present invention, it has been determined that a stent of the present invention which is not fully expanded to the final predetermined diameter by inflation of the balloon catheter will continue to expand following withdrawal of the balloon and thereby support the interior wall of the blood vessel. Because the stent of the present invention has been educated to have a memory of the final desired diameter, it exhibits little to no negative recoil following implantation into the target site.

DETAILED DESCRIPTION OF THE INVENTION

Definitions:

"Bioresorbable polymer" as used herein refers to a polymer whose degradation by-products can be bio-assimilated or excreted via natural pathways in a human body.

"Crimping" as used herein refers to a process that involves radial pressing on a polymeric cylindrical device having slits, or openings in the wall thereof in order to allow a decrease in the diameter of the device without substantially affecting the thickness of the wall or struts of the cylindrical device. Such process, typically also results in an increase in length of the cylindrical device.

"Degradable polymer" as used herein refers to a polymer that breaks down into monomers and oligomers when placed in a human body or in an aqueous solution and maintained under conditions of temperature, osmolality, pH, etc., that mimic physiological media preferably without involving enzymatic degradation in order to minimize the risk of triggering the antigenantibody defense system of the human body.

"Final predetermined shape and diameter" as used herein refers to the desired diameter, length, design and wall thickness of a stent that has been deployed to a target site in a vessel, particularly a blood vessel, duct, or tube in a mammalian subject, particularly a human subject.

"Negative recoil" as used herein refers to an undesirable decrease in diameter of an expanded stent.

"Positive recoil" as used herein refers to an increase in diameter of a stent that has been educated to have a desired final diameter but has not been fully expanded to the desired final diameter.

"Relaxation-related recoil" as used herein refers to the slow change in dimensions of a polymeric device due to a time-dependent slow rearrangement of molecule conformations according to a well known behavior of viscoelastic polymeric matters. Such rearrangement is due to thermal agitation that slowly leads the polymeric material to a thermodynamic equilibrium typical of the storage conditions when it has been processed under different environmental conditions. Relaxation is very slow below Tg, i.e. when the matter is in the glassy state.

"Tg" or "glass transition temperature" as used herein refers to the temperature at which a polymer changes from a rubbery state to a glassy state and vice versa.

In one aspect the present invention provides an assembly which can be used to deliver a polymer-based stent to a region in the lumen of a tube, duct, or vessel of a mammalian subject, particularly a human subject. The assembly comprises an inflatable balloon catheter and a polymeric stent that when expanded to a final predetermined shape and diameter exhibits little to no negative recoil. Thus, the assembly is particularly useful for delivering the stent of the present invention to a lesion in the blood vessel of a human subject who has undergone PTC angioplasty.

The polymeric stent of the present invention is snugly mounted on the balloon catheter and has an internal diameter that matches the external diameter of the deflated balloon catheter, and is less than the final predetermined diameter so that the stent assembly can be easily inserted and passed through a tube, vessel or duct of the subject. The polymeric stent of the present invention is stably disposed on the balloon catheter such that the stent does not expand when stored at room temperature or when inserted into the blood vessel of a mammalian subject, particularly a human subject. Although not necessary, the present assembly also, optionally, comprises a retractable sheath disposed on the exterior surface of the polymeric stent.

I. Stent

The stent of the present assembly is formed from a degradable and bioresorbable polymer having a Tg at least 8 degrees above 37° C., preferably at least 20 degrees above 37° C. The polymer that fauns the walls of the stent can be a homopolymer or a copolymer. Preferably, the polymer is totally amorphous in order to minimize the risk of formation of tiny inflammatory crystalline residues during degradation. The chains of the polymer are not cross-linked. However, light cross-liking is acceptable provided that thermal and viscoelastic characteristics that allow education, crimping, and deployment of the device are maintained. In certain embodiments, the polymer has a Tg of from about 45° C. to about 120° C. Examples of the types of polymers that are suitable for the stent of the present invention include, but are not limited to, lactic acid-based stereocopolymers (PLAx copolymers composed of L and D units, where X is the percentage of L-lactyl units) (55<Tg<60), copolymers of lactic and glycolic acids (PLAxGAy, where X, the percentage of L-lactyl units, and Y, the percentage of glycolyl units, are such that the Tg of the copolymer is above 45° C.), and Poly(lactic-co-glycolic-co-gluconic acid) where the OH groups of the gluconyl units can be more or less substituted (PLAx-GAyGLx, where X, the percentage of L-lactyl units, and Y, the percentage of glycolyl units, and Z the percentage of gluconyl units are such that the Tg of the terpolymer is above 45° C.). Other suitable polymers include, but are not limited to, polylactic acid (PLA), polyglycolic acid (PGA) polyglactin (PLAGA copolymer), polyglyconate (copolymer of trimethylene carbonate and glycolide, and a copolymer of polyglycolide or lactide acid or polylactic acid with .epsilon.-caprolactone), provided that the polymer has a Tg of at least 45° C. or greater.

The stent of the present assembly is a cylindrical device having a first open end, a second open end, a channel connecting the first and second open ends, and slits, or openings in the walls of the cylindrical device. Such slits or openings allow crimping of the polymeric cylindrical device from a larger diameter to a smaller diameter without substantially altering the thickness of the wall of the device, as well as expansion of the polymeric cylindrical device from a smaller diameter, e.g. the crimped diameter, to a larger diameter without substantially altering the thickness of the wall upon inflation of a balloon catheter that is disposed inside the cylindrical device. Such slits or openings may be formed by standard processing techniques such as by molding, cutting, engraving or photolithography.

The polymeric cylindrical device is formed by standard techniques such as extrusion, molding, spinning, injection molding or any other processing technique that transforms the brut polymer into a hollow cylindrical device. Although less desirable, the cylindrical device can also be formed by knitting polymer threads or fibers, provided that the stitches are then fused together to form a continuous polymeric network in which the slits, or openings are formed by the voids between the stitches. The initial polymeric cylindrical device that is formed by any of these processes can be configured to have the final predetermined shape, length, wall thickness and diameter, all of which are tailored to the application for which the stent is to be utilized. For example, for cardiovascular applications the initial polymeric device that is formed by these processes can have a final predetermined length ranging from 0.5 cm to approximately 3 cm. For certain applications, the initial polymeric cylindrical device can have a final, predetermined diameter ranging from 0.50 mm to 8.0 mm with a final, predetermined wall thickness ranging from 0.05 to 0.5 mm. Alternatively, the initial cylindrical device that is formed by any of these processes can have a smaller diameter than the final predetermined diameter.

Stents of the present invention can be formulated so as to be able to carry and deliver a variety of materials or bioactive agents, provided that these materials or agents do not form a solid solution with the polymer and do not act as a plasticizer that decreases the Tg of the polymeric device below 45° C. Such materials include, but are not limited to, opacifying agents, natural agents, and pharmaceutical agents. The polymer can be admixed with such materials or agents. For example, the material or bioactive agent may be incorporated into the polymeric cylindrical device as a solid dispersion in a matrix. The matrix can be formed with a dispersion of uniform particles in the biocompatible polymeric materials of the type hereinbefore described in connection with the stent of the present invention. Such particles must be small enough not to affect the continuity of the matrix, e.g., one fifth to one tenth the strut or wall thickness of the cylindrical device. The materials or bioactive agents may also be deposited on the exterior or interior surface of the cylindrical device either by impacting or chemical coupling.

Stents of the present invention lack memory of previous processing and have a memory of the final predetermined shape and diameter.

II. Preparation of the Polymer-Based Stent Assembly

In another aspect, the present invention relates to a method of preparing the present polymer-based stent and stent assembly. In those instances where the initial polymeric cylindrical device has a smaller diameter than the final predetermined diameter, slits or openings are formed in the cylindrical device as described above, and then the cylindrical device is deformed or expanded to the final shape and diameter. This can be achieved by inserting a balloon into the polymeric cylindrical device (referred to hereinafter as a "pre-cut cylindrical device"), heating the pre-cut cylindrical device to a temperature at or above the Tg of the polymer that is used to form the pre-cut cylindrical device, and inflating the balloon to a size approximately equal to or slightly greater than the final predetermined interior diameter of the implanted stent. While maintaining the expanded pre-cut cylindrical device at the final predetermined shape, size, and diameter, such as by mounting the pre-cut cylindrical device on a solid support, the pre-cut cylindrical device is educated to erase any former process-related memory and to acquire a memory of the final predetermined shape, size and diameter. In those instances where the initial cylindrical device is formed at the final predetermined shape, size, and diameter, such deformation or expansion step is not required. In those instances where the initial cylindrical device is formed at the final predetermined shape, size, and diameter, slits or openings in the cylindrical device can be made prior to or after the education step as described below.

While it is at the final predetermined shape, size, and diameter, the cylindrical device is educated by heating the device to a temperature sufficiently above the Tg of the polymer from which the device is formed and for a time sufficient to erase any former process-related memory and to impart a new memory of the final predetermined shape and diameter to the polymeric cylindrical device. It is believed that such conditions allow the polymer chains to relax and reorganize themselves from an entanglement typical of the former processing stages to an entanglement typical of the high temperature at which the cylindrical device is educated. This last entanglement is frozen by quenching (fast cooling to room temperature or below). In those cases where the polymeric cylindrical device initially is at a diameter that is less than the final predetermined diameter, heating to a temperature well above the Tg of the polymer erases not only the anisotropic internal stresses promoted by the extrusion or molding process during which the polymeric chains are more or less oriented and quenched heterogeneously by contact with the cold atmosphere or the cold mold, but also the former processing-related memory of the polymer chains. Good results have been obtained by heating a laser-precut polymeric cylindrical device fowled from PLA75 and deformed from a diameter of 1.0 mm to 4 mm at a temperature of 80° C. for 30 minutes. It is expected that temperatures of from about 45° C. to about 120° C. and times of 5 minutes or more will be suitable for educating stents made from PLAx with 0≤X≤100, PLAxGAy with 0≤X≤25 and 75≤Y≤100, or any PLAxGAyGLz.

While still in its expanded state, the cylindrical device is then quenched or cooled to a temperature below the Tg of the polymer, preferably to room temperature, more preferably below room temperature. Such cooling step is performed at a rate sufficiently rapid to stiffen the cylindrical device into its new shape, and sufficiently slow to allow the whole polymer mass to reach equilibrium at a temperature below the Tg without chain relaxation taking place. Given the thinness of the stent, this time is relatively short compared to the time during which the polymeric tube is educated.

The educated, polymeric cylindrical device is then mounted on a deflated balloon catheter and uniformly crimped to reduce its diameter and facilitate introduction of the stent assembly of the present invention into a vessel, duct, or tube of a mammalian subject, particularly a human subject. During crimping, the diameter of the cylindrical device is reduced by a suitable amount from the educated size, as for example by 100 to 400 percent. The crimping involves heating the educated cylindrical device to a temperature sufficient to allow deformation of the polymeric matrix without erasing the memory that has been imparted to the device during the education step. Thus, during crimping the educated cylindrical device is heated to a temperature at or slightly above the Tg of the polymer, while evenly applying pressure to the exterior surface of the cylindrical device. Good results have been obtained by heating the cylindrical device to a temperature 5° C. above the Tg of the polymer. Such crimping step substantially uniformly reduces the diameter of the cylindrical device such that it fits snugly on the balloon. Simultaneously, the crimping step also increase the length of the cylindrical device provided that the design allows the compression of the slits, openings, or voids and the arrangement of the struts of the cylindrical device close to each other. To quench the polymer matrix of the cylindrical device, the stent assembly is then rapidly cooled to a temperature below the Tg of the polymer, preferably to room temperature, more preferably to a temperature below room temperature, while maintaining pressure on the exterior surface of the cylindrical device. The final product is a stent assembly comprising an inflatable balloon catheter having a snug fitting polymeric stent stably disposed thereon. As used herein the phrase "stably disposed thereon" means that the stent will not expand under normal storage conditions, i.e., while stored at room temperature or below room temperature, or during the short period of time allowed to the clinician to insert the assembly into a vessel of a mammalian subject.

III. Procedures for Determining Times and Temperatures for Educating and Crimping the Stent of the Present Invention.

Temperatures and times suitable for educating the cylindrical device and for thereby developing a stent resistant to relaxation-related recoil can be assessed by inflating the balloon catheter of the present stent assembly to the final predetermined diameter, removing the balloon catheter after deflation and storing the expanded stent at 37° C. If the stent exhibits little to no recoil when stored under these conditions for 4 to 6 weeks or, preferably the time estimated for an artery wall to recover from PTC angioplasty, the times and temperatures employed for educating the stent are suitable. In those cases where the polymeric stent exhibits a small amount of recoil, the cylindrical device can be educated at a diameter slightly larger than the final predetermined diameter in order to compensate for the small amount of negative recoil.

Temperatures and times suitable for crimping the stent to a reduced diameter can be assessed by allowing the stent-mounted balloon catheter of the present assembly to stay at room temperature or at the storage temperature. If the crimped stent stays collapsed at the small diameter corresponding to the deflated balloon under these conditions, the times and temperatures employed during crimping are suitable.

IV. Deployment of the Stent.

The polymer-based stent assembly of the present invention is introduced into a duct, tube, or vessel, e.g., a blood vessel of a mammalian subject, preferably in conjunction with a guiding catheter, and advanced to a target site, e.g., the site of stenotic lesion. After it is located at the target site the balloon is rapidly inflated thereby causing expansion of the stent to its final desired diameter or slightly below its final diameter. Optionally, the inflation fluid, balloon and stent are heated to a temperature above body temperature to aid in expansion.

During this process the diameter of the stent increases, but the thickness of the walls of the stent remain substantially the same.

EXAMPLES

The following examples contained herein are intended to illustrate but not limit the invention.

Example 1

A polymeric tube was formed from PLA75 (Mw of approximately 130,000, Mw/Mn=1.8, as determined by Size Exclusion Chromatography, Tg approximately 58° C.) by extrusion through a dye interior/exterior of 1.2/1.4 mm diameter. Slits were then cut into the extruded tube using a femtosecond pulsed laser according to a design permitting expansion of the small diameter polymeric cylindrical device without changing wall thickness. The small diameter cylindrical device was mounted onto a deflated 4 mm balloon, heated to 65° C. in a heating bath, and expanded to 4 mm by inflating the balloon. The resulting assembly was then rapidly cooled to about room temperature. The balloon was removed, and a 4 mm stainless steel support was inserted into the cylindrical device to lock the device into its final pre-determined diameter and shape. In order to erase any memory of previous processing and to impart a memory of this final diameter and shape to the cylindrical device, the device, mounted on the stainless steel support, was heated in an 80° C. pre-heated oven for 30 minutes. Thereafter, the educated, cylindrical device was rapidly cooled to room temperature by inserting the device in running water at a temperature of 20° C., while the device was still mounted on the support. The cooling has an effect of stiffening the polymeric device. The newly shaped stent was then mounted on a new, deflated, balloon and both the balloon and the stent were then heated to 65° C., a temperature high enough to allow deformation of the device but not high enough to allow the chains to reorganize in a short period of time, and then the stent was crimped on the balloon by applying equal pressure to the exterior surface of the stent. The stent was crimped on the deflated balloon by using a standard system, which is typically used for the crimping of metallic stents. Such system applies equal radial pressure to the exterior surface of the device. Once the diameter was reduced to a size small enough to obtain a snug fit on the deflated balloon, the pressure was maintained while the contracted, mounted stent was rapidly cooled to stiffen the stent in the crimped shape and reduced diameter. This stiffening ensured a snug fit of the stent on the balloon.

Example 2

A polymeric tube was formed from PLA75 (Mw of approximately 130,000, Mw/Mn=1.8, as determined by Size Exclusion Chromatography, Tg approximately 55° C.) by extrusion through a dye interior/exterior of 4.0/4.2 mm diameter. Void spaces were then cut into the extruded tube using a femtosecond pulsed laser according to a design which permits contraction of the resulting educated, polymeric cylindrical device to a smaller diameter without modifying wall thickness. A 4 mm stainless steel support was inserted into the cylindrical device to lock the device into the final desired diameter and shape. In order to erase any memory of previous processing and to impart a memory of this final diameter and shape to the cylindrical device, the device, mounted on the stainless steel support, was heated in an 80° C. pre-heated oven for 30 minutes. Thereafter, the educated, cylindrical device was rapidly cooled to room temperature by inserting the device in running water at a temperature of 20° C., while the device was still mounted on the support. The cooling has an effect of stiffening the polymer device. The educated stent was then mounted on a new, deflated, balloon and both the balloon and the stent were then heated to 65° C. a temperature sufficiently high to allow deformation of the device but not high enough to allow the chains to reorganize. The stent was then crimped on the balloon by applying equal pressure to the exterior surface of the stent. Once the diameter of the stent was reduced to a size small enough to obtain a snug fit on the deflated balloon, the pressure was maintained while the contracted, mounted stent was rapidly cooled to stiffen the stent in the crimped shape and reduce diameter. This stiffening ensured a snug fit of the stent on the balloon.

Example 3

A polymeric tube was formed from PLA50 (Mw of approximately 145,000, Mw/Mn=1.6, as determined by Size Exclusion Chromatography, Tg approximately 58° C.) by extrusion through a dye interior/exterior of 1.2/1.4 mm diameter. The tube was processed as described above in example 1 to provide a stent assembly of the present invention.

Example 4

A polymeric tube was formed from PLA50 (Mw of approximately 145,000, Mw/Mn=1.6, as determined by Size Exclusion Chromatography, Tg approximately 55° C.) by extrusion through a dye interior/exterior of 4.0/4.2 mm diameter. The tube was processed as described above in example 2 to provide a stent assembly of the present invention.

Example 5

A polymeric tube was formed from PLA62.5 (Mw of approximately 165,000, Mw/Mn=1.7, as determined by Size Exclusion Chromatography, Tg approximately 56° C.) by extrusion through a dye interior/exterior of 1.2/1.4 mm diameter. The tube was processed as described above in example 1 to provide a stent assembly of the present invention.

Example 6

A polymeric tube was formed from PLA62.5 (Mw of approximately 165,000, Mw/Mn=1.7, as determined by Size Exclusion Chromatography, Tg approximately 56° C.) by extrusion through a dye interior/exterior of 4.0/4.2 mm diameter. The tube was processed as described above in example 2 to provide a stent assembly of the present invention.

Example 7

A polymeric tube was formed from PLA96GA4 (Mw of approximately 185,000, Mw/Mn=1.8, as determined by Size Exclusion Chromatography, Tg approximately 51° C.) by extrusion through a dye interior/exterior of 1.2/1.4 mm diameter. The tube was processed as described above in example 1 to provide a stent assembly of the present invention.

Example 8

A polymeric tube was formed from PLA96GA4 (Mw of approximately 185,000, Mw/Mn=1.8, as determined by Size Exclusion Chromatography, Tg approximately 51° C.) by extrusion through a dye interior/exterior of 4.0/4.2 mm diameter. The tube was processed as described above in example 2 to provide a stent assembly of the present invention.

Stents made as described in examples 1-8 were expanded to the final predetermined diameter and stored at room temperature in a liquid environment for more than 3 months did not exhibit negative recoil.

From the foregoing it can be seen that there has been provided a stent, an assembly comprising an inflatable balloon and the present stent, and a method for use thereof which has numerous advantages. Because the present stent has a memory of a final predetermined shape and diameter, it exhibits little to no relaxation-related recoil when implanted into a vessel of a mammalian subject. Moreover, when expanded by mechanical stress to a diameter less than the final predetermined diameter, the present stent may exhibit positive recoil and adaptation to the geometry of the vessel in which it is deployed. The stents of the present invention can be formulated and/or treated so as to carry materials and bioactive agents to the target site.

What is claimed is:

1. A degradable and bioresorbable polymeric stent that is substantially resistant to relaxation-related negative recoil when expanded mechanically to a final predetermined diameter in a lumen of a tube, duct, or vessel of a mammalian subject, said polymeric stent being formed by the following steps:
    (a) heating a polymeric stent, which is at the final predetermined diameter to a temperature sufficiently above the Tg of a polymeric material that forms said polymeric stent, for a time sufficient to erase memory of previous processing of said polymeric stent; and
    wherein said polymeric stent has a wall defining a first open end, a second open end, and a channel connecting said first and second open ends;
    wherein said polymeric stent is mounted on a solid support for maintaining said polymeric stent at the final predetermined diameter;
    (b) rapidly cooling said polymeric stent at a temperature below the Tg of the polymeric material to quench said polymeric stent and provide a polymeric stent that lacks any former process-related memory and has a memory of the final predetermined diameter.

2. The polymeric stent of claim 1, further comprising the step of:
    (c) forming slits, voids, or open spaces in the wall of said polymeric stent prior to step (a) or after step (b) to provide a polymeric stent that is substantially resistant to relaxation-related negative recoil when mechanically expanded to the final predetermined diameter by inflation of a balloon that has been inserted into said channel of said polymeric stent and implanted in the lumen of a tube, duct, or vessel of a mammalian subject or stored at 37° C. for 4 weeks or more.

3. The polymeric stent of claim 1, wherein said polymeric stent is prepared before it is mounted on a balloon catheter.

* * * * *